(12) United States Patent
Ronci

(10) Patent No.: US 6,620,158 B2
(45) Date of Patent: Sep. 16, 2003

(54) METHOD OF HAIR REMOVAL

(76) Inventor: Romeo V. Ronci, 15 Viscount Rd., Warwick, RI (US) 02889

(*) Notice: Subject to any disclaimer, the term of this patent is extended or adjusted under 35 U.S.C. 154(b) by 0 days.

(21) Appl. No.: 10/368,453

(22) Filed: Feb. 20, 2003

(65) Prior Publication Data
US 2003/0125723 A1 Jul. 3, 2003

Related U.S. Application Data

(63) Continuation-in-part of application No. 09/662,212, filed on Sep. 14, 2000, now abandoned.

(51) Int. Cl.[7] .............................................. A61B 18/18
(52) U.S. Cl. ............................ 606/36; 606/43; 606/133
(58) Field of Search ........................ 606/36, 43, 133, 606/134; 604/20; 128/898

(56) References Cited

U.S. PATENT DOCUMENTS

| | | | |
|---|---|---|---|
| 2,888,927 A | | 1/1959 | Fozard |
| 4,155,363 A | * | 5/1979 | Letchworth et al. .......... 606/36 |
| 4,498,474 A | | 2/1985 | Chalmers et al. |
| 4,598,709 A | | 7/1986 | Smith et al. |
| 4,821,717 A | | 4/1989 | Wehrli |
| 5,026,369 A | | 6/1991 | Cole |
| 5,470,332 A | | 11/1995 | Mehl, Sr. et al. |
| 5,868,738 A | * | 2/1999 | Mehl, Sr. ........................ 606/36 |
| 6,063,076 A | * | 5/2000 | Mehl et al. ................... 606/134 |

OTHER PUBLICATIONS

Global Electrolysis Supply, TransdermalTutorial, www.global–electrolysis–supply.com/TransdermalTutorial.htm, Canada, undated, 13 pages.
International Hair Removal System, Inc., Manual for Transdermal Electrolysis System, Southern Pines, North Carolina, undated, 8 pages.
R.A. Fischer Co., "Hair Conductivity Tests", www.rafischer.com/hairtest.htm, undated, 7 pages.
Removatron International, Manual for Removatron electrolysis machine, Boston, Massachusetts, undated, 10 pages.

* cited by examiner

Primary Examiner—Michael Peffley
(74) Attorney, Agent, or Firm—Richard C. Litman

(57) ABSTRACT

The method for hair removal applies an electrolytic procedure, followed sequentially by a thermolytic procedure. The electrolytic method involves preparing the area to be treated by allowing silver/silver chloride gel to remain on the area for a period long enough to allow the electrolyte gel to diffuse through the skin, then applying a cotton swab to a galvanic probe and swabbing circles of the electrolyte gel about the treatment area while applying galvanic current for two passes about the area. Then the hair is grasped by tweezers before removing the electrolyte gel from the area, and an RF current is applied through the tweezers for twenty to twenty-five seconds while gently pulling the hair.

15 Claims, 4 Drawing Sheets

METHOD OF HAIR REMOVAL

CROSS REFERENCES TO RELATED APPLICATIONS

This is a continuation-in-part of my prior application Ser. No. 09/662,212, filed Sep. 14, 2000, now abandoned.

BACKGROUND OF THE INVENTION

1. Field of the Invention

The present invention relates to a method of hair removal, and more particularly to a method of hair removal which involves the sequential application of an electrolytic procedure followed by a thermolytic procedure.

2. Description of the Related Art

Many people suffer from unwanted hair growth on their face or their body. While some depilatories and laser hair removal treatments offer temporary relief, various other techniques have been developed in an effort to provide for permanent hair removal. In general, these techniques have proved to be either painful, or ineffective in producing permanent hair removal.

Techniques for permanent hair removal generally fall into one of three categories: electrolytic, thermolytic, or a blend of electrolytic and thermolytic techniques. As used in the present application, the term "electrolytic", as applied to a method of hair removal, refers to a technique in which a galvanic or direct current (dc) is directed to the papilla of a hair in order to initiate a chemical reaction in which water and salt in the cell tissue surrounding the hair follicle are electrolyzed, so that sodium hydroxide is formed. The sodium hydroxide, being caustic, destroys the papilla, resulting in permanent hair removal.

As used in the present application, the term "thermolytic" refers to a method of permanent hair removal in which a high frequency, or radio frequency (RF), current is applied to the hair or hair follicle. The RF current generates heat, which destroys the hair follicle.

As used in the present application, the "blend" refers to a method of permanent hair removal which involves the simultaneous application of the electrolytic and thermolytic methods. This may be accomplished by modulating an RF current on a direct current bias.

Several devices illustrate variations on one or more of these methods. U.S. Pat. No. 4,155,363, issued May 22, 1979 to Letchworth et al., describes a machine which provides a constant direct current to a plurality of filament (wire needle) electrodes, regardless of the electrical load. The machine is also capable of providing pulsed direct current, or of reversing the polarity of the direct current. U.S. Pat. No. 4,598,709, issued Jul. 8, 1986 to Smith et al., discloses a machine which is capable of delivering either a direct current only, a high frequency RF current only, or a blend of galvanic and RF current through a wire needle probe. U.S. Pat. No. 4,821,717, issued Apr. 18, 1989 to J. M. M. Wehrli, teaches a barbed needle which can be used with either the electrolytic, thermolytic, or blend methods.

The foregoing patents have described devices which use an invasive technique for permanent hair removal, i.e., they all involve the insertion of a needle through the skin closely adjacent the hair follicle. Several patents describe devices directed towards non-invasive techniques for hair removal.

U.S. Pat. No. 2,888,927, issued Jan. 2, 1959 to E. M. Fozard, describes a method of hair removal which uses an RF current directed through a pair of tweezers which are used to grasp the hair to be removed. U.S. Pat. No. 4,498,474, issued Dec. 12, 1985 to Chalmers et al., teaches an epilation method which involves applying one, or preferably two, wetting fluids to the skin surrounding the hair, the wetting solutions having an ionic activity equivalent to at least 25 ppm sodium chloride in water, followed by applying an RF current to the hair through tweezers.

U.S. Pat. No. 5,026,369, issued Jun. 25, 1991 to H. L. Cole, discloses an electrolytic method of hair removal which involves applying a saline type electrode solution comprising 85% glycerin, 14% water, 0.5% salt, and 0.5% copper sulphate to the hair, and then applying a direct or galvanic current to the hair through tweezers. A series of patents issued to T. L. Mehr, Sr., and to Mehr et al., including U.S. Pat. No. 5,470,332, issued Nov. 28, 1995, U.S. Pat. No. 5,868,738, issued Feb. 9, 1999, and U.S. Pat. No. 6,063,076, issued May 16, 2000, teach techniques for removing multiple hairs simultaneously using either electrolytic, thermolytic, or blend techniques. The '332 patent teaches application of a multiple layer material, including a non-conductive adhesive layer against the skin, a conductive adhesive layer above the first layer, and a structural layer above the conductive layer. The '738 patent adds disclosure concerning wetting the hair with a liquid solution and using a comb to remove, multiple hairs. The '076 patent describes a conductive layer which also includes a cold wax material.

International Hair Removal System, Inc. of Southern Pines, N.C., markets Transdermal Electrolysis machines, originally based on the '369 patent issued to Cole, discussed above. The manual for the device has been changed to indicate the device comes with a cotton swab probe holder. The manual describes a revised procedure in which the area is pretreated with an electrode gel (presumably the same gel described in the Cole patent) for five to ten minutes, depending on skin color. The gel is wiped off and the skin is dried, then the gel is applied in ¼ inch circles separated by ¼ inch. A cotton swab probe dipped in water is applied to barely touch the skin without moving the probe while a direct current is applied through the probe. The treatment is repeated twice for each circle, the gel is removed, and a tweezers is used to manually grasp and remove the hair. The Transdermal Electrolysis manual does not teach the use of silver/silver chloride electrode gel, nor sequentially treating the hair with a thermolytic method.

Removatron International of Boston, Mass. markets a thermolytic machine which supplies an RF current applied through tweezers. The manual teaches cleaning the area with alcohol, applying a wet towel to the area for 30–60 seconds to soften the skin, drying the skin, and using tweezers to grasp the hair while applying RF current, then pulling the tweezers to remove the hair.

Global Electrolysis Supply of Canada provides both high and low viscosity silver/silver chloride gels, as well as a stylet holder and probe stylet for use with their Aavexx model Transdermal Electrolysis machines. According to the Transdermal Tutorial web pages published, at least on Jan. 3, 2003, at http://www.global-electrolysis-supply.com, Global Electrolysis teaches the use of a low frequency (~60 Hz) current of 2,500 to 5,000 $\mu$a at ~115V.

It is noted that recent studies have cast doubt on the efficacy of the use of tweezers for permanent hair removal. Early theory suggested that a current applied through the tweezers would travel down the hair to the papilla, where the electrolytic chemical reaction would take place. However, in Hair Conductivity Tests conducted by R. A. Fischer Co. Mar. 17–26, 1998 and reported at www.rafischer.com/hairtest.htm, test results show that hair is a non-conductor.

The reference suggests that methods which employ tweezers are only effective if a suitable electrolyte gel is applied to the hair fiber.

None of the above inventions and patents, taken either singly or in combination, is seen to describe the instant invention as claimed. Thus a method of hair removal solving the aforementioned problems is desired.

SUMMARY OF THE INVENTION

The method for hair removal of the present invention applies an electrolytic procedure, followed sequentially by a thermolytic procedure. The electrolytic method involves preparing the area to be treated by allowing silver/silver chloride gel to remain on the area for a period long enough to allow the electrolyte gel to diffuse through the skin, then applying a cotton swab to a galvanic probe and swabbing circles of the electrolyte gel about the treatment area while applying galvanic current for two passes about the area. Then the hair is grasped by tweezers before removing the electrolyte gel from the area, and an RF current is applied through the tweezers for twenty to twenty-five seconds while gently pulling the hair.

In performing the method, the electrolyte is chosen for high conductivity. A silver/silver chloride gel has been found to be effective. The gel should be allowed to diffuse through the skin for a period which is long enough to allow the gel to penetrate to the papilla. Prior methods have been ineffective, in part, for failure to allow sufficient time for transport of the electrolyte to the papilla. Immediately prior to application of the galvanic probe, the gel should be applied to the area in ¼" circles separated by about ¼", and a swab moistened with the gel is applied to the galvanic probe. The swab is used to massage each circle with a circular motion, in turn, while applying the galvanic current, then the swab is applied to each circle in the same fashion for a second time. On the first pass, water and salt near the hair undergo electrolysis to form sodium hydroxide. Any remaining water in the follicle is drawn out to dilute the sodium hydroxide, but this additional water is electrolyzed to form additional sodium hydroxide on the second pass, the increased concentration of sodium hydroxide helping to ensure destruction of the papilla.

Subsequent treatment with RF current applies heat to ensure destruction of the follicle. The remaining electrolyte on the hair and diffused through the skin ensures conduction of the current to the papilla, so that heat is generated in the tissue adjacent the papilla for destruction of the papilla and permanent hair removal. The entire procedure is noninvasive, thereby eliminating the pain associated with prior electrolytic and thermolytic methods which required the use of needles. The sequential application of the electrolytic and thermolytic methods has been found to be more effective that electrolytic methods alone, thermolytic methods alone, or simultaneous blending of electrolytic and thermolytic methods.

Accordingly, it is a principal object of the invention to provide a method for permanent hair removal which is more effective than conventional methods of permanent hair removal through the sequential application of electrolytic and thermolytic methods.

It is another object of the invention to provide an effective, noninvasive method for permanent hair removal in order to avoid pain associated with epilation methods which involve the use of needles.

It is a further object of the invention to provide a method for permanent hair removal which makes effective use of an electrolytic gel for both electrolytic and thermolytic processes by providing sufficient time for the electrolyte to diffuse through the skin to the papilla.

Still another object of the invention is to provide a method for permanent hair removal which employs a silver/silver chloride electrolyte in both electrolytic and thermolytic procedures for improved conductivity.

It is an object of the invention to provide improved elements and arrangements thereof for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The present invention is a method of hair removal which is noninvasive and which involves the application of an electrolysis procedure, followed sequentially by a thermolytic procedure.

Figure 1:
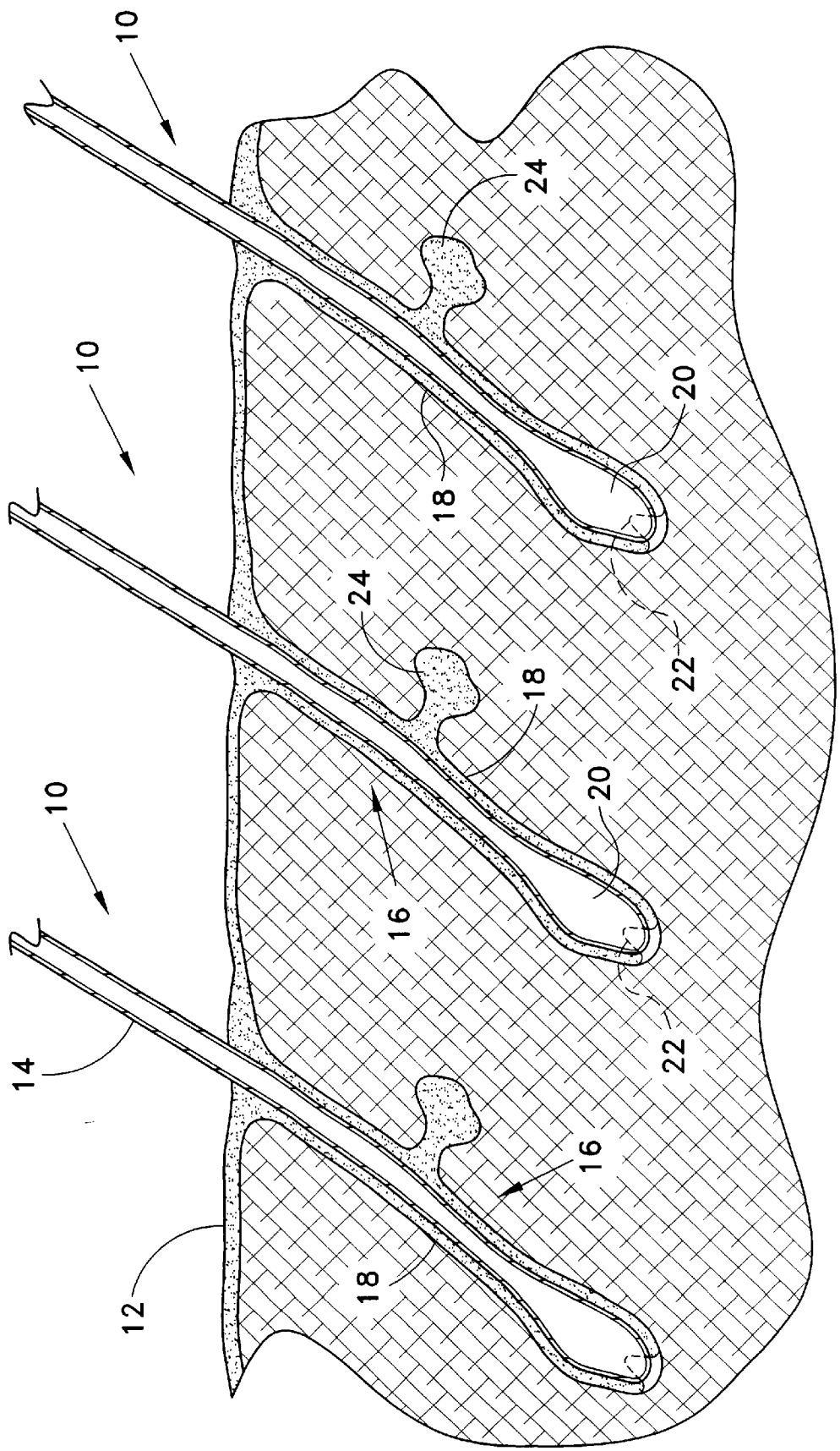
FIG. 1 is a diagrammatic view showing the structure of a human hair follicle and the surrounding tissue.

Referring to FIG. 1, a hair 10 generally consists of a portion above the skin 12, referred to as the shaft 14, and a portion below the skin 12, referred to as the root 16. The tissue around the hair 10 forms an involutional fold called the follicle 18, which is sometimes referred to as a tube in which the hair 10 grows. The base of the root 16 is enlarged, and forms what is called the hair bulb 20. At the base of the follicle 18 a nipple shaped vascular protrusion referred to as the papilla 22 extends into the bulb 20 and supplies the growing hair with nutrients. Branching to one side of the follicle 18 is one or more sebaceous glands 24, which secrete oil into the follicle 18. Also connected to the follicle 18 are nerves (not shown) which, e.g., cause the skin to raise the hair erect or stand up in cold weather, due to fright, etc.

The hair 10 goes through a growth cycle. The first stage, or anagen phase, is the growth phase when a new hair is formed and begins to extend out of the follicle 18 and above the epidermis 12. The length of the anagen phase is variable, depending in part on the area of the body. A hair in the facial area may remain in the anagen phase for approximately two to three weeks. The anagen phase is followed by the catagen phase in which the papilla 22 recedes and the bulb 20 breaks away from the papilla 22. The catagen phase may be as brief as one to two days. The catagen phase is followed by the telogen, or resting, phase, in which the bulb 20 has broken away from the papilla 22 and no longer receives nourishment. The telogen phase may last anywhere from a few days to years. The hair 10 is retained in the follicle 18 by strands of fibrous or connective tissue extending between the root 16 and the walls of the follicle 18, but is subject to falling out, being pushed out when a new hair starts growing in the follicle 18, or being pulled out.

Methods for permanent hair removal are generally believed to be effective only when the hair 10 is in the anagen phase. Removal of hair in the catagen or telogen phase only provides temporary relief, since the papilla 22 is not affected. During the telogen phase, the follicle 18 has dried out and does not have sufficient salt or water to generate the sodium hydroxide necessary for destruction of the papilla 22. Methods for permanent hair removal focus on destruction of the matrix, or connection between the papilla 22 and the bulb 20, during the anagen phase.

According to the method of hair removal of the present invention, the patient first undergoes an electrolytic procedure. The patient is instructed to prepare for the procedure by adequate hydration (two to three glasses of water) on the day of treatment. The patient should avoid caffeine, alcohol or smoking.

The area to be treated is cleansed with alcohol or an antiseptic lotion to remove dirt or grease, and the area is steamed by application of a warm, moist towel to the area for about two minutes to open the pores. An electrode gel, preferably a silver ion/silver chloride gel, is applied to the area to be treated using a cotton swab. The gel is allowed to remain on the skin for a period of time sufficient to allow the electrolyte to diffuse through the skin and into the follicles. The importance of allowing sufficient time for this to occur is important to the method, as electrolytic methods sometimes fail because of insufficient transport of the electrolyte across the barrier of the skin. An exemplary average time period is ten to fifteen minutes. For light, fair skin complexion, the time period may be in the lower end of the range. For dark or leathery skin, more time may be required, e.g., fifteen to twenty minutes.

Figure 2:
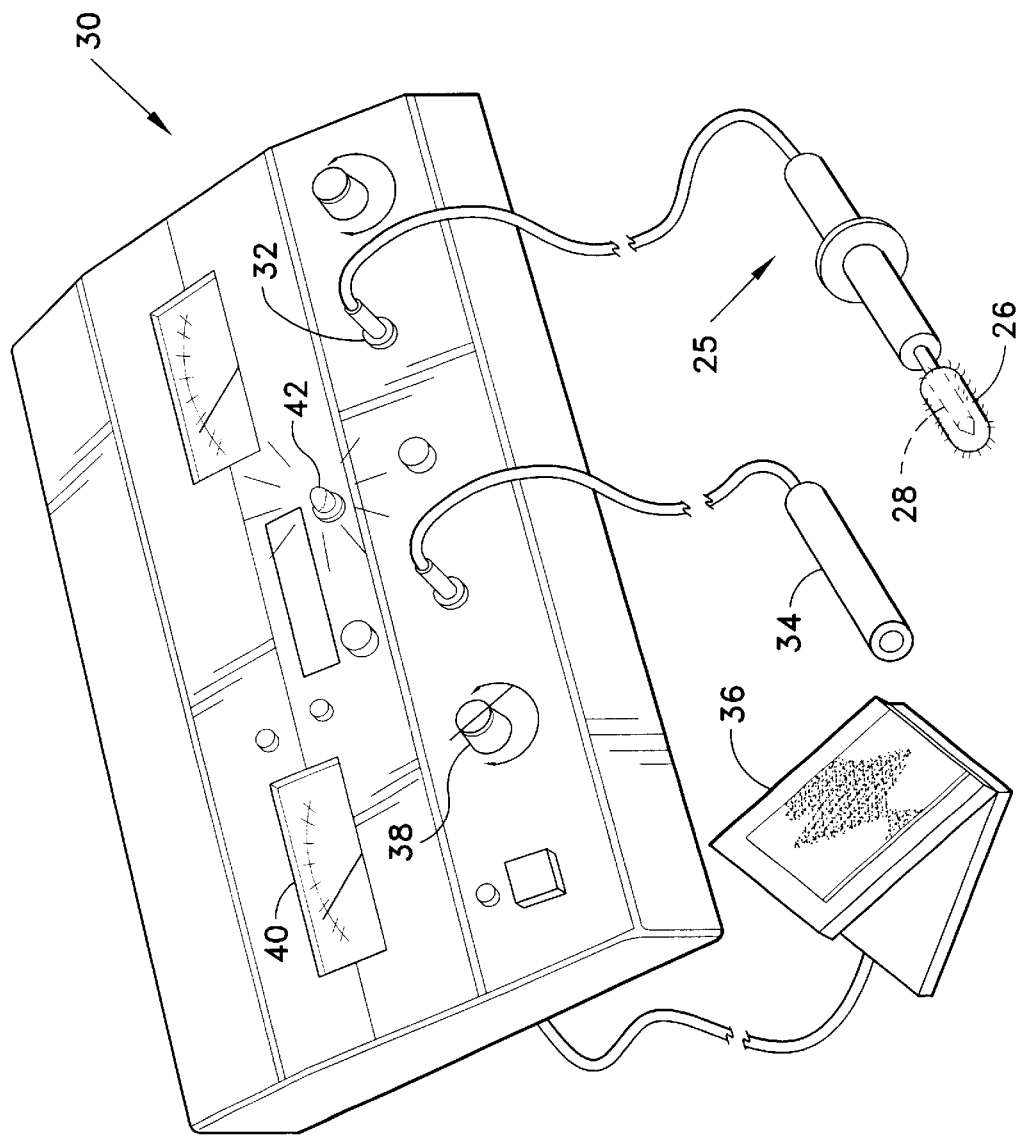
FIG. 2 is a perspective view of a galvanic electrolysis machine with a cotton swab probe attached to the machine.

During this time period a cotton swab probe 24 is prepared by breaking a cotton swab (paper stem only) to a length of about ¾" and placing the swab 26 on the end of a metal probe or stylet holder 28 with the tip of the swab 26 in contact with the end of the metal probe 28. The cotton swab 26 is saturated with silver/silver chloride gel. The probe 24 is attached to an electrolysis machine 30 capable of delivering a galvanic current as shown in FIG. 2.

An exemplary galvanic machine 30 is a Transdermal System Model TD 729 or TD 829. The unit is capable of delivering 500–2500 microamperes (the TD 829 is capable of delivering 500 $\mu a$ more than the TD 729) of current at between 100–380 volts dc. The unit includes a jack 32 for attachment of the cotton swab probe 24 (or tweezers), a ground electrode 34 which may be grasped by the patient, a foot pedal switch 36 for closing the circuit for any desired time period, and associated controls 38, meters 40, indicators 42, and timers, as is known in the art.

Figure 3:
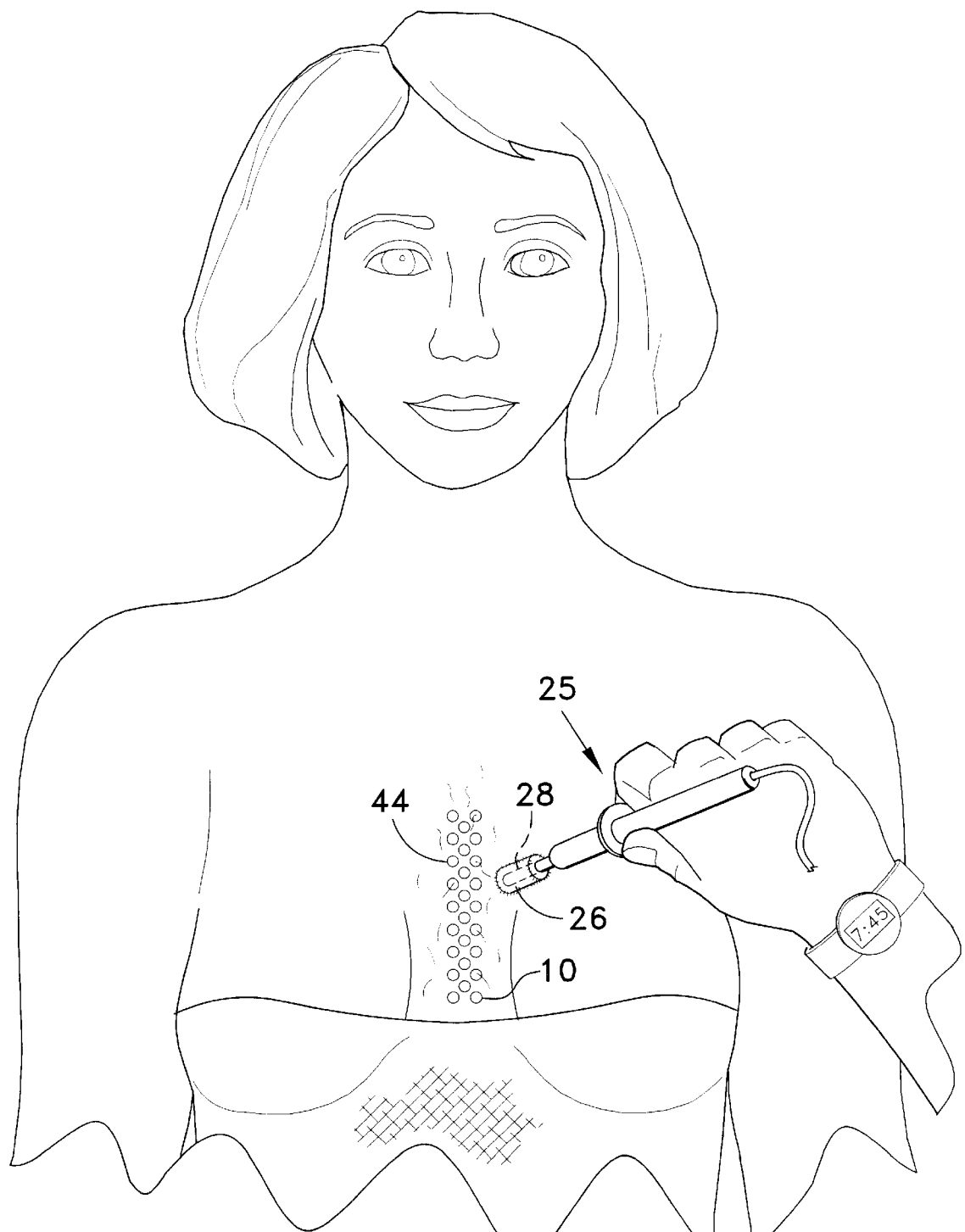
FIG. 3 is an environmental, perspective view showing a pattern of electrolyte gel applied to a patient's chest and application of the cotton swab probe to the gel.

After the gel has remained on the skin for the prescribed period, any excess is wiped from the area to be cleaned. Silver/silver chloride electrode gel is then applied to the area to be treated in a pattern of circles 44, as shown in FIG. 3. The gel circles 44 are applied in a diameter of between about ¼" to ½", with each circle 44 being separated from adjacent circles by about ¼" to ½". Preferably the circles 44 are applied in staggered rows. The cotton swab probe 24 is applied to each circle 44, in turn, moving the probe tip in a slow circular motion while depressing the foot pedal 36 to apply a galvanic current to the gel. The machine 30 should be programmed to deliver about 1,500 to 3,000 $\mu a$ for twenty to twenty-five seconds. Current is delivered at a low intensity and gradually increased to the maximum that the patient can tolerate within the prescribed range. The machine 30 sounds a buzzer at the end of the programmed time period.

After treating each gel circle 44 in the pattern, the process is repeated a second time so that current has been applied to each gel circle 44 twice during the session. The reason for the second application of galvanic current to the gel circles 44 is that on the first pass, water and salt near the hair 10 undergo electrolysis to form sodium hydroxide. Any remaining water in the follicle 18 is drawn out to dilute the sodium hydroxide, but this additional water is electrolyzed to form additional sodium hydroxide on the second pass, the increased concentration of sodium hydroxide helping to ensure destruction of the papilla 22. Upon completion of the second pass, each circle 44 should be joined to an adjacent circle or circles to ensure complete coverage of the treatment area.

Upon completion of the electrolytic procedure described above, the hair 10 is subjected to a thermolytic procedure. The thermolytic procedure involves grasping the hair 10 with tweezers 46 (shown in FIG. 4) and applying an RF current of about ten watts to the hair 10 for about twenty to twenty-five seconds. The electrolytic procedure has severed most of the connection of the bulb 20 to the papilla, and the heat generated by the RF current completes destruction of the matrix by coagulating and drying the papilla 22. The thermolytic procedure is performed before cleaning excess electrolyte gel from the treatment area, so that the electrolyte serves to conduct the RF current to the base of the follicle 18. The hair 10 can then be removed by gently pulling the hair 10 with the tweezers 46.

Figure 4:
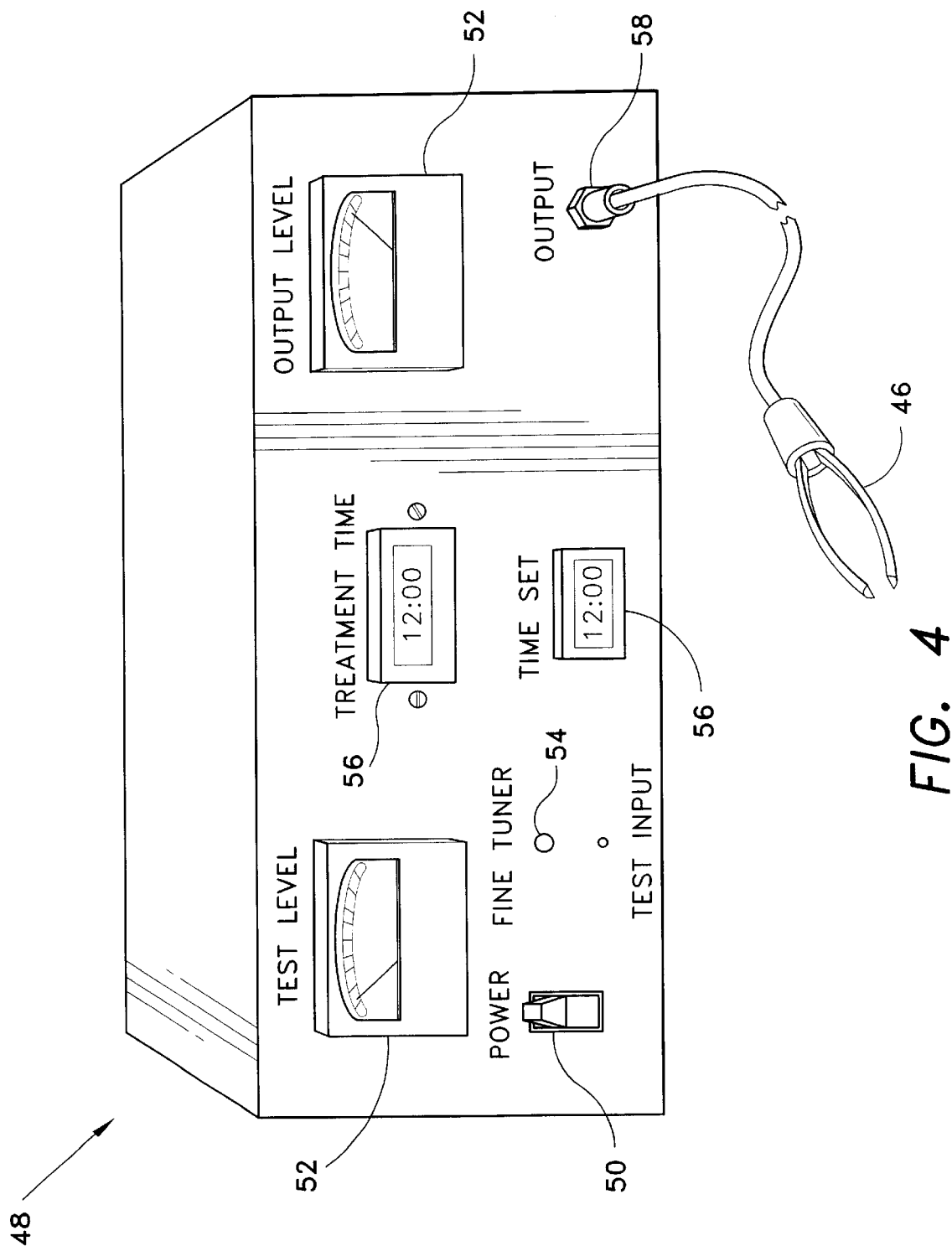
FIG. 4 is a perspective view of a thermolytic electrolysis machine with tweezers attached to the machine.

FIG. 4 shows a representative machine 48 for delivering the RF current. The machine includes a power switch 50, appropriate meters 52, indicators 54, timer displays 56, controls, and a jack 58 for connecting the tweezers 46 to the machine 48. Machines for delivering an RF current to tweezers 46 for thermolytic epilation procedures are well known in the art, and will not be described further. A representative machine 48 is manufactured by Removatron International of Boston, Mass., which is capable of delivering up to forty-five watts of RF current (above one MHz).

After removal of the hairs from the treatment area, the skin is cleaned with a warm face cloth and a lotion is applied to the skin. The patient should return for repeat treatments every seven days for the next ten to twelve weeks, and thereafter the patient should undergo further treatment whenever new hair is first noticed in the treatment area.

It is important to the method that the electrolyte gel has high conductivity. Silver/silver chloride gel marketed by Global Electrolysis Supply of Canada has been found suitable for this purpose. It is further of importance that the electrolyte gel is allowed to remain on the skin for a sufficient period of time to penetrate to the base of the follicle before application of the galvanic current. Finally, it is important to the method that the tweezers and RF current be applied to the hair while the hair and treatment area are still moist with the electrolyte gel in order to provide a conduction path to the base of the follicle for the RF current.

The steps in the method of hair removal according to the present invention may be briefly summarized as follows: applying a highly conductive electrolyte gel to an area to be treated; waiting for a period of time sufficient to permit the electrolyte gel to penetrate to a base of any hair follicles in the treatment area; wiping the electrolyte gel from the treatment area; applying electrolyte gel to the treatment area in rows of staggered circles; attaching a cotton swab saturated in the electrolyte gel to a probe tip to form a cotton swab probe; conducting a galvanic electric current through the cotton swab probe while touching each of the electrolyte gel circles with the cotton swab probe in turn; repeating the previous step so that current has been applied to each of the gel circles twice; after two applications of galvanic current to the circles, grasping each of the hairs in the treatment area with tweezers while applying an RF current through the tweezers, the hairs in the treatment area still being moist with electrolyte gel; and gently pulling each of the hairs immediately after applying the RF current to the hair in order to remove the hair.

It will be seen that the method of the present inventions provides a painless, noninvasive procedure for permanent hair removal. It has been found that the forgoing procedure provides for more effective, permanent hair removal than noninvasive electrolytic methods alone, noninvasive thermolytic methods alone, or blend methods of hair removal.

It is to be understood that the present invention is not limited to the embodiments described above, but encompasses any and all embodiments within the scope of the following claims.

I claim:

1. A method of hair removal, comprising the steps of:
   (a) applying a highly conductive electrolyte gel to a skin surface of an area having hairs to be removed;
   (b) waiting for a period of time sufficient to permit the electrolyte gel to penetrate to a base of hair follicles of the hairs to be removed;
   (c) conducting a galvanic electric current through the electrolyte gel in order to electrolyze water and salt in the follicles to form sodium hydroxide;
   (d) after step (c), grasping each of the hairs to be removed with tweezers while applying an RF current through the tweezers, the hairs in the treatment area still being moist with electrolyte gel, in order to apply heat to the base of the hair follicles; and
   (e) gently pulling each of the hairs immediately after applying the RF current to the hair in order to remove the hair.

2. The method of hair removal according to claim 1, wherein the electrolyte gel consists essentially of silver/silver chloride electrolyte gel.

3. The method of hair removal according to claim 1, further comprising the step of attaching a cotton swab saturated in the electrolyte gel to a probe tip to form a cotton swab probe, step (c) being performed with the cotton swab probe.

4. The method of hair removal according to claim 1, further comprising the step of applying the electrolyte gel to the treatment area in rows of circles, step (c) further comprising conducting the galvanic current through each of the circles in sequence for a first pass through all of the circles, and then conducting the galvanic current through each of the circles in sequence for a second pass through all of the circles in order to concentrate the sodium hydroxide formed and remove water from the base of the follicles.

5. The method of hair removal according to claim 1, further comprising the step of steaming the area to be treated in order to open pores in the skin before step (a).

6. The method of hair removal according to claim 1, wherein step (b) further comprises waiting for a period of time of between about ten to twenty minutes for the electrolyte gel to penetrate to the hair follicles.

7. The method of hair removal according to claim 1, wherein the galvanic current applied in step (c) is between about 1,500 and 3,000 microamperes.

8. A method of hair removal, comprising the steps of:
   (a) applying a highly conductive electrolyte gel to an area to be treated;
   (b) waiting for a period of time sufficient to permit the electrolyte gel to penetrate to a base of any hair follicles in the treatment area;
   (c) wiping the electrolyte gel from the treatment area;
   (d) applying the electrolyte gel to the treatment area in rows of circles;
   (e) attaching a cotton swab saturated in the electrolyte gel to a probe tip to form a cotton swab probe;
   (f) conducting a galvanic electric current through the cotton swab probe while touching each of the electrolyte gel circles with the cotton swab probe in turn;
   (g) repeating step (f) so that the current has been applied to each of the gel circles twice;
   (h) after step (g), grasping each of the hairs in the treatment area with tweezers while applying an RF current through the tweezers, the hairs in the treatment area still being moist with electrolyte gel; and
   (i) gently pulling each of the hairs immediately after applying the RF current to the hair in order to remove the hair.

9. The method of hair removal according to claim 8, further comprising the step of steaming the area to be treated in order to open pores in the treatment area before step (a).

10. The method of hair removal according to claim 8, wherein step (b) further comprises waiting for a period of time of between about ten to twenty minutes for the electrolyte gel to penetrate to the hair follicles.

11. The method of hair removal according to claim 8, wherein the electrolyte gel consists essentially of silver/silver chloride electrolyte gel.

12. The method of hair removal according to claim 8, wherein step (d) further comprises forming the circles to have a diameter of between about one-quarter of an inch to one-half of an inch.

13. The method of hair removal according to claim 8, wherein step (d) further comprises positioning the gel circles about one-quarter of an inch to one-half inch apart.

14. The method of hair removal according to claim 8, wherein step (d) further comprises applying the circles in staggered rows.

15. The method of hair removal according to claim 8, wherein the galvanic current applied in step (f) is between about 1,500 and 3,000 microamperes.

* * * * *